US011486723B2

(12) United States Patent
Misaki et al.

(10) Patent No.: US 11,486,723 B2
(45) Date of Patent: Nov. 1, 2022

(54) INFORMATION PROCESSING DEVICE, INFORMATION PROCESSING METHOD, AND NON-TRANSITORY STORAGE MEDIUM

(71) Applicant: TOYOTA JIDOSHA KABUSHIKI KAISHA, Toyota (JP)

(72) Inventors: Masahiro Misaki, Nagoya (JP); Orie Mitsuhashi, Kasugai (JP); Masahiro Ueda, Nisshin (JP); Yoshitaka Atsumi, Toyota (JP); Naoto Sasagawa, Nishio (JP); Naoki Yamamuro, Nagoya (JP); Chiho Ogawa, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 203 days.

(21) Appl. No.: 16/581,835

(22) Filed: Sep. 25, 2019

(65) Prior Publication Data

US 2020/0096357 A1   Mar. 26, 2020

(30) Foreign Application Priority Data

Sep. 25, 2018   (JP) ............................ JP2018-179126

(51) Int. Cl.
*G01C 21/36* (2006.01)
*G06Q 30/02* (2012.01)
(Continued)

(52) U.S. Cl.
CPC ........ *G01C 21/3617* (2013.01); *A61B 5/7282* (2013.01); *B60W 40/08* (2013.01);
(Continued)

(58) Field of Classification Search
CPC ............ G01C 21/3617; G01C 21/3641; A61B 5/7282; B60W 40/08; B60W 2040/0872;
(Continued)

(56) References Cited

U.S. PATENT DOCUMENTS 9,751,534 B2 * 9/2017 Fung .................... G06V 10/764
9,988,055 B1 * 6/2018 O'Flaherty ............ G08B 21/06
(Continued)

FOREIGN PATENT DOCUMENTS

JP      2001108477 A  *  4/2001
JP      2001108477 A     4/2001
(Continued)

*Primary Examiner* — Luis A Martinez Borrero
(74) *Attorney, Agent, or Firm* — Oliff PLC

(57) ABSTRACT

An information processing device is provided with a controller which executes: obtaining predetermined service information including an advertisement; obtaining predetermined user information on biological information of a user in a vehicle in which the user rides; estimating a health condition of the user based on the user information; extracting distribution information which is information, among the service information, is judged to match the user based on the user's health condition, and which is information about a medical facility according to the health condition or/and information about a predetermined store which sells goods according to the health condition; and selecting, based on position information of the vehicle, information to be actually distributed to the user from among the distribution information thus extracted, and providing the information thus selected to the user, by transmitting the selected distribution information to an on-board device of the vehicle.

5 Claims, 11 Drawing Sheets

(51) Int. Cl.
  *A61B 5/00* (2006.01)
  *B60W 40/08* (2012.01)
(52) U.S. Cl.
  CPC ..... *G01C 21/3641* (2013.01); *G06Q 30/0266* (2013.01); *B60W 2040/0872* (2013.01)
(58) Field of Classification Search
  CPC ...... B60W 50/14; B60W 50/10; B60W 30/12; G06Q 30/0266
  See application file for complete search history.

(56) References Cited

U.S. PATENT DOCUMENTS

| | | | | |
|---|---|---|---|---|
| 10,156,848 | B1 * | 12/2018 | Konrardy | G06Q 30/0284 |
| 10,160,457 | B1 * | 12/2018 | O'Flaherty | G08B 21/06 |
| 10,235,998 | B1 * | 3/2019 | Khaleghi | G06V 40/174 |
| 10,327,705 | B2 * | 6/2019 | Weidl | A61B 5/48 |
| 10,573,314 | B2 * | 2/2020 | Khaleghi | G10L 25/78 |
| 10,729,378 | B2 * | 8/2020 | Lerner | A61B 5/0533 |
| 10,832,148 | B2 * | 11/2020 | Kochura | G06N 5/048 |
| 2014/0309893 | A1 * | 10/2014 | Ricci | B60R 25/20 701/1 |
| 2014/0344062 | A1 * | 11/2014 | Lamont | G06Q 30/0267 705/14.64 |
| 2016/0001781 | A1 * | 1/2016 | Fung | G16H 50/20 701/36 |
| 2017/0255966 | A1 * | 9/2017 | Khoury | B60W 40/00 |
| 2018/0157980 | A1 * | 6/2018 | Kochura | G06N 5/048 |
| 2018/0322941 | A1 * | 11/2018 | Krishnan | G16H 40/63 |
| 2018/0330804 | A1 * | 11/2018 | Hiruta | A61B 5/6893 |
| 2019/0267003 | A1 * | 8/2019 | Khaleghi | B60K 28/06 |
| 2019/0391581 | A1 * | 12/2019 | Vardaro | A61B 5/02055 |

FOREIGN PATENT DOCUMENTS

| | | | | |
|---|---|---|---|---|
| JP | 2012-120597 A | | 6/2012 | |
| JP | 2016193165 A | | 11/2016 | |
| JP | 2018060336 A | * | 4/2018 | |
| JP | 2018060336 A | | 4/2018 | |
| KR | 20180016026 A | * | 8/2016 | ........ A61B 2505/00 |
| KR | 20180016026 A | * | 2/2018 | ........ G06Q 30/0251 |

* cited by examiner

| ADVERTISEMENT ID | FACILITY ID | LOCATION | GENRE | ADVERTISEMENT INFORMATION |
|---|---|---|---|---|
| A001 | 20A | a | MEDICAL FACILITY | ... |
| A002 | 20B | b | SUPERMARKET | ... |
| A003 | 20C | c | PHARMACY | ... |
|  |  |  |  |  |

Fig. 4A

| ADVERTISEMENT ID | ADVERTISEMENT INFORMATION |
|---|---|
| A001 | ○○ HOSPITAL: PLEASE CONSULT IF YOU SUFFER FROM LOWER BACK PAIN |
| A002 | ×× SUPERMARKET: HAVING FRESH FOOD SALE NOW |
| A003 | △△ PHARMACY: HAVING SALES CAMPAIGN FOR MAGNETIC THERAPEUTIC DEVICES NOW |

Fig. 4B

| ITEM | CONDITION |
|---|---|
| HEART RATE | 70 |
| BLOOD PRESSURE | 120 / 80 |
| BLOOD FLOW | POOR |
| BODY TEMPERATURE | 36.5°C |
| SWEAT AMOUNT | ○○ |
| BODY WEIGHT | 90kg |
| RIDING POSTURE | BAD |
|  |  |

Fig. 5

| ADVERTISEMENT ID | FACILITY ID | LOCATION | GENRE | ADVERTISEMENT INFORMATION |
|---|---|---|---|---|
| A001 | 20A | a | MEDICAL FACILITY | ○○ HOSPITAL: PLEASE CONSULT IF YOU SUFFER FROM LOWER BACK PAIN |
| A003 | 20C | c | PHARMACY | △△ PHARMACY: HAVING SALES CAMPAIGN FOR MAGNETIC THERAPEUTIC DEVICES NOW |
| | | | | |

Fig. 6

INFORMATION PROCESSING DEVICE, INFORMATION PROCESSING METHOD, AND NON-TRANSITORY STORAGE MEDIUM

CROSS REFERENCE TO THE RELATED APPLICATION

This application claims the benefit of Japanese Patent Application No. 2018-179126, filed on Sep. 25, 2018, which is hereby incorporated by reference herein in its entirety.

BACKGROUND

Technical Field

The present disclosure relates to an information processing device, an information processing method, and a non-transitory storage medium.

Description of the Related Art

In patent literature 1, there is disclosed a technique in which in cases where it is diagnosed that the health condition of an occupant of a vehicle is abnormal, information on candidates for the name of a disease, and those facilities which can treat a disorder corresponding to the name of the disease is provided to the occupant.

CITATION LIST

Patent Literature

Patent Literature 1: Japanese patent application laid-open publication No. 2012-120597

SUMMARY

The present disclosure has for its object to provide a technique that can promote to guide a user riding on a vehicle to a facility according to the health condition of the user.

An information processing device according to the present disclosure may include a controller comprising at least one processor configured to execute:

obtaining predetermined service information including an advertisement;

obtaining predetermined user information on biological information of a user in a vehicle in which the user rides;

estimating a health condition of the user based on the user information;

extracting distribution information which is information, among the service information, is judged to match the user based on the user's health condition, and which is information about a medical facility according to the health condition or/and information about a predetermined store which sells goods according to the health condition; and selecting, based on position information of the vehicle, information to be actually distributed to the user from among the distribution information thus extracted, and providing the information thus selected to the user, by transmitting the selected distribution information to an on-board device of the vehicle.

The present disclosure can also be grasped from the aspect of an information processing method. For example, the present disclosure may be an information processing method in which a computer executes:

a step of obtaining predetermined service information including an advertisement;

a step of obtaining predetermined user information on biological information of a user in a vehicle in which the user rides;

a step of estimating a health condition of the user based on the user information;

a step of extracting distribution information which is information, among the service information, is judged to match the user based on the user's health condition, and which is information about a medical facility according to the health condition or/and information about a predetermined store which sells goods according to the health condition; and a step of selecting, based on position information of the vehicle, information to be actually distributed to the user from among the distribution information thus extracted, and providing the information thus selected to the user, by transmitting the selected distribution information to an on-board device of the vehicle.

The present disclosure may be a non-transitory storage medium in which a program for causing a computer to execute such an information processing method is stored.

According to the present disclosure, it is possible to promote to guide a user riding on a vehicle to a facility according to the health condition of to the user.

BRIEF DESCRIPTION OF THE DRAWINGS

FIG. 4A is a view illustrating an example of a service information table according to the embodiment.

FIG. 4B is a view illustrating an example of another service information table according to the embodiment.

FIG. 5 is a view illustrating an example of a user information table according to the embodiment.

FIG. 6 is a view illustrating an example of a distribution information table according to the embodiment.

DESCRIPTION OF THE EMBODIMENTS

In an information processing device which is one mode of the present disclosure, a controller may extract information (distribution information) about a medical facility according to the health condition of a user, or/and a predetermined store which sells goods according to the user's health condition, among predetermined service information including an advertisement. According to this, the information matching the health condition of this user can be provided to the user. However, although the distribution information is only provided to the user as it is, there is a possibility that the user may not be fully promoted to go to the medical facility or the predetermined store that sends the distribution information.

Then, the controller may select the information to be actually distributed to the user from among the extracted distribution information, based on the position information of a vehicle, and provide this information to the user by transmitting the selected distribution information to an on-board device of the vehicle. According to this, the user will be provided with the information which matches the health condition of the user, and which is relevant to facilities (medical facilities, predetermined stores, etc.) existing in an area where the user can drop in the facilities relatively easily. Accordingly, the information processing device according to the present disclosure can promote to guide the user to a facility which sends the service information matching the user's health condition.

Hereinafter, specific embodiments of the present disclosure will be described with reference to the drawings. The sizes, materials, shapes, relative layouts and the like of the components described in the following embodiments are not intended to limit the technical scope of the disclosure to these alone, unless otherwise specified.

First Embodiment (System Configuration)

Figure 1:
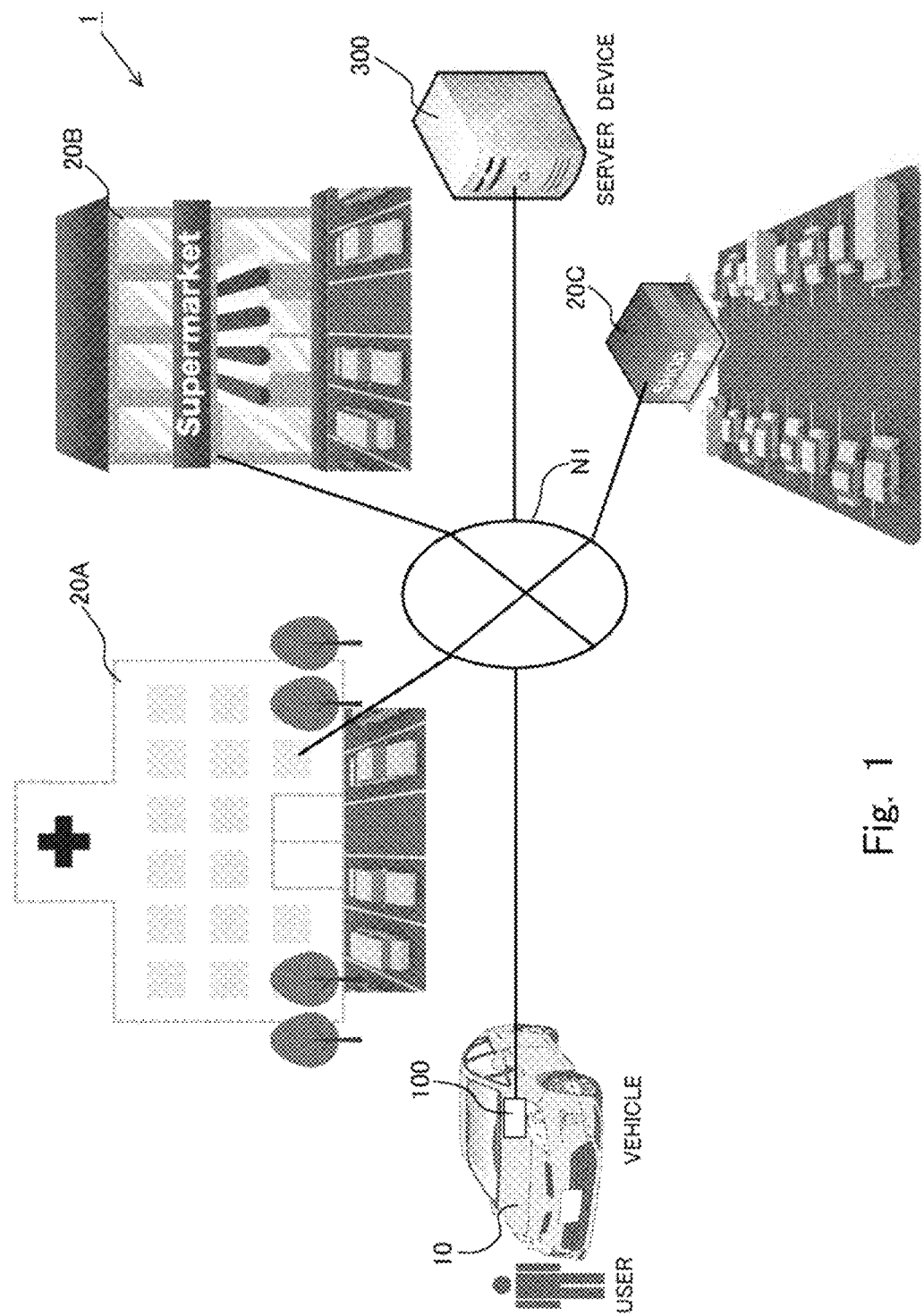
FIG. 1 is a view illustrating the schematic configuration of an advertisement provision system according to an embodiment.

FIG. 1 is a diagram showing a schematic configuration of an advertisement providing system according to the present embodiment. In the example of FIG. 1, the advertisement providing system 1 includes a vehicle 10, facilities 20 A-20 C, and a server device 300. The vehicle 10 is a vehicle on which a user who uses the advertisement providing system 1 rides, and includes an on-board device 100. Each of the facilities 20 A to 20 C includes a facility-side terminal 200.

In the advertisement providing system 1, the on-board device 100, the facility-side terminal 200, and the server device 300 are connected to each other via a network N1. For example, as the network N1, a wide area network (WAN), which is a worldwide public communication network such as the Internet, or other communication networks may be adopted. Furthermore, the network N1 may include a mobile communication network for mobile phones, or a wireless communication network such as Wi-Fi.

The staff or the like of the facilities 20 A to 20 C can input predetermined service information including advertisements by using the respective facility-side terminals 200. In addition, predetermined user information relating to biological information of the user riding on the vehicle 10 is input to the on-board device 100 via a sensor or the like described later. The information is transmitted to the server device 300 via the network N1.

The server device 300 executes a process of providing distribution information matching the user based on the information. Details of the processing will be described later.

(Hardware Configuration)

Figure 2:
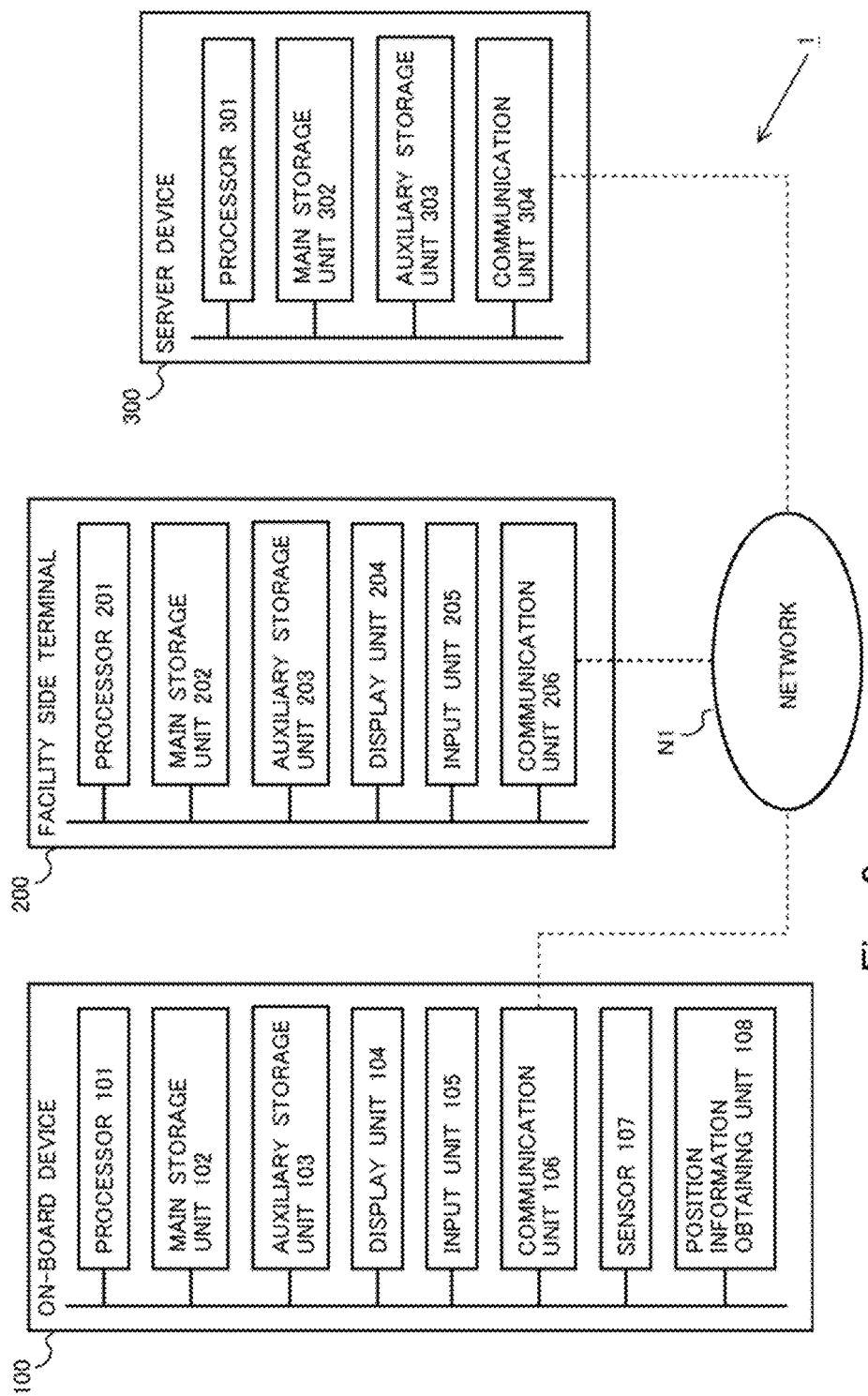
FIG. 2 is a view exemplifying the hardware configuration of each of an on-board device, a facility side terminal, and a server device in the advertisement provision system.

FIG. 2 is a diagram illustrating hardware configurations of the on-board device 100, the facility-side terminal 200, and the server device 300.

First, the server device 300 will be described. The server device 300 has a general computer configuration. The server device 300 includes a processor 301, a main storage unit 302, an auxiliary storage unit 303, and a communication unit 304. These are connected to each other by a bus. The main storage unit 302 and the auxiliary storage unit 303 are computer-readable recording media. The hardware configuration of the computer is not limited to the example shown in FIG. 2, and components may be omitted, replaced, or added as appropriate.

In the server device 300, the processor 301 loads the program stored in the recording medium into the work area of the main storage unit 302, executes the program, and controls each functional component and the like through the execution of the program, thereby realizing a function that matches a predetermined purpose.

The processor 301 is, for example, a CPU (Central Processing Unit) or a DSP (Digital Signal Processor). The processor 301 controls the server device 300 and performs various information processing operations. A main storage unit 302 includes, for example, a RAM (Random Access Memory) and a ROM (Read Only Memory). An auxiliary storage unit 303 is, for example, a EPROM (Erasable Programmable ROM or a hard disk drive (HDD or Hard Disk Drive). The auxiliary storage unit 303 may include a removable medium, that is, a portable recording medium. The removable medium is, for example, a USB (Universal Serial Bus) memory or a disc recording medium such as a CD (Compact Disc) or a DVD (Digital Versatile Disc).

The auxiliary storage unit 303 stores various programs, various data, and various tables in a recording medium in a readable and writable manner. The auxiliary storage unit 303 stores an operating system (OS), various programs, various tables, and the like. The information stored in the auxiliary storage unit 303 may be stored in the main storage unit 302. The information stored in the main storage unit 302 may be stored in the auxiliary storage unit 303.

The communication unit 304 is connected to other devices and controls communication between the server device 300 and other devices. The communication unit 304 is, for example, a LAN (Local Area Network) interface board, and wireless communication circuits for wireless communication. The LAN interface board and the wireless communication circuit are connected to a network N1 such as the Internet, which is a public communication network.

The series of processing executed by the server device 300 may be executed by hardware or software.

Next, the on-board device 100 will be described. The on-board device 100 includes a processor 101, a main storage unit 102, an auxiliary storage unit 103, a display unit 104, an input unit 105, a communication unit 106, a sensor 107, and a position information obtaining unit 108. The processor 101, the main storage unit 102, and the auxiliary storage unit 103 are the same as the processor 301, the main storage unit 302, and the auxiliary storage unit 303 of the server device 300, and therefore descriptions thereof are omitted. The display unit 104 is, for example, an LCD (Liquid Crystal Display), an EL (Electroluminescence) panel, or the like. The input unit 105 includes a touch panel, a push button, and the like. The input unit 105 may include a camera that enables input of video or images or an input unit of sound such as a microphone. The communication unit 106 is communication means for connecting the vehicle 10 to a network. The communication unit 106 accesses the network N1 using, for example, a telephone communication network such as a cellular telephone or the like, or radio communication such as the WiFi, and can perform communication with the server device 300 or the like.

The sensor 107 is means for sensing biological information of the user riding on the vehicle 10. The sensor 107 senses the heart rate, the blood pressure, the blood flow, the body temperature, the sweat amount, the body weight, the image of the face or the riding posture of the user, and the like as the biological information of the user. The sensor 107 for sensing the heart rate, the blood pressure, the blood flow, the body temperature, and the sweat amount of the user is, for example, a well-known device which is embedded in a steering wheel and is capable of sensing these. The sensor 107 for sensing an image of the user's face or riding posture is, for example, a camera installed in the vehicle 10.

The position information obtaining unit 108 is a means for obtaining the current position of the vehicle 10, and typically includes a GPS receiver or the like.

Next, the facility side terminal 200 will be described. The facility-side terminal 200 is a personal computer (PC) connected to the server device 300 via a network N1 such as the Internet, which is a public communication network.

Similar to the on-board device 100, the facility-side terminal 200 includes a processor 201, a main storage unit 202, an auxiliary storage unit 203, a display unit 204, an input unit 205, and a communication unit 206. The processor 201, the main storage unit 202, the auxiliary storage unit 203, the display unit 204, the input unit 205, and the communication unit 206 are the same as the processor 101, the main storage unit 102, the auxiliary storage unit 103, the display unit 104, the input unit 105, and the communication unit 106 of the on-board device 100, and therefore descriptions thereof are omitted. In the facility-side terminal 200, the input unit 205 may include a keyboard, a mouse, and the like.

(Functional Configuration of Server Device)

Figure 3:
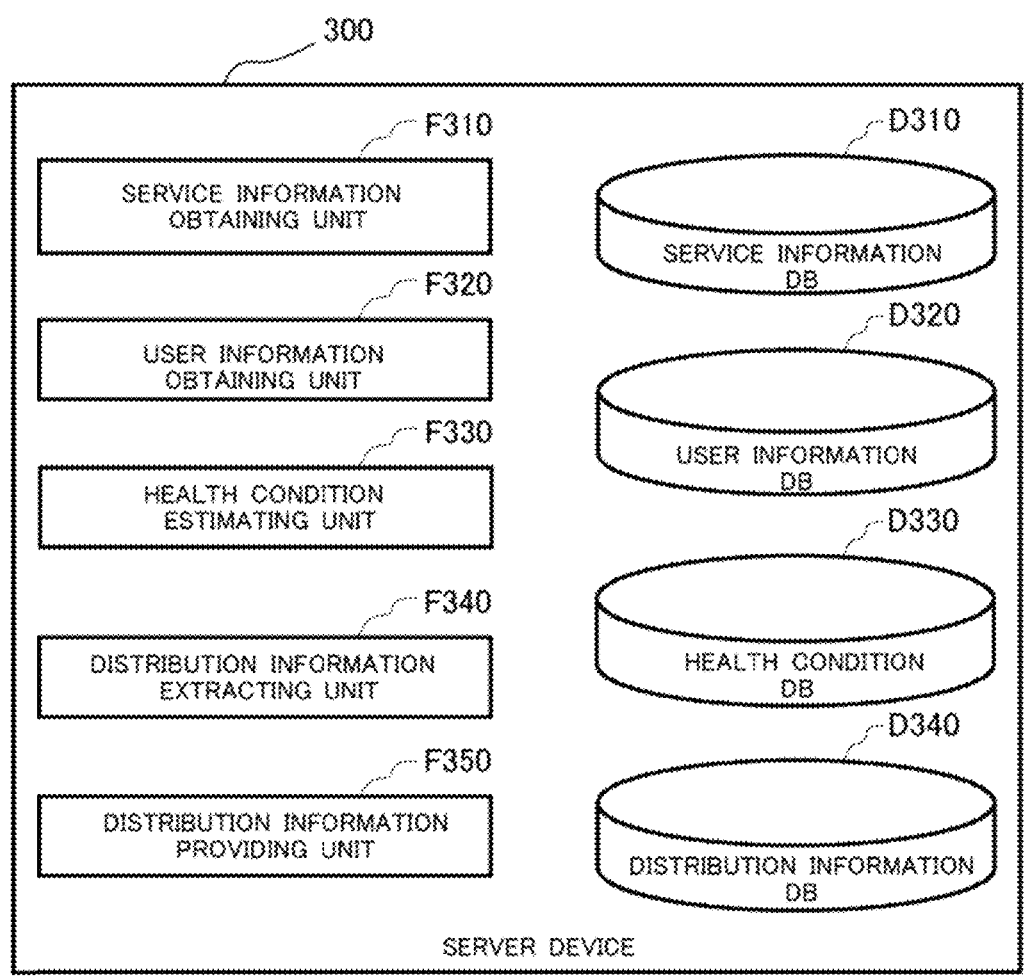
FIG. 3 is a view exemplifying the functional configuration of the server device according to the embodiment.

FIG. 3 is a diagram illustrating a functional configuration of the server device 300. The server device 300 includes, as functional components, a service information obtaining unit F310, a user information obtaining unit F320, a health condition estimating unit F330, a distribution information extracting unit F340, a distribution information providing unit F350, a service information database D310, a user information database D320, a health condition database D330, and a distribution information database D340. The processor 301 of the server device 300 executes the processes of the service information obtaining unit F310, the user information obtaining unit F320, the health condition estimating unit F330, the distribution information extracting unit F340, and the distribution information providing unit F350 by the computer programs in the main storage unit 302. However, any of the functional components or a part of the processing thereof may be executed by a hardware circuit.

The service information database D310, the user information database D320, the health condition database D330, and the distribution information database D340 are constructed by managing the data stored in the auxiliary storage unit 303 by programs of the database management systems (DBMS) executed by the processor 301. The service information database D310, the user information database D320, the health condition database D330, and the distribution information database D340 are, for example, relational databases.

It should be noted that any of the functional components of the server device 300 or a part of the processing thereof may be executed by another computer connected to the network N1. For example, the processing of the distribution information providing unit F350 and the processing of the services information obtaining unit F310, the user information obtaining unit F320, the health condition estimating unit F330, and the distribution information extracting unit F340 may be executed by separate computers.

The service information obtaining unit F310 obtains predetermined service information including advertisements (hereinafter, also referred to simply as "service information"). Then, the service information obtaining unit F310 registers the obtained service information in the service information database D310.

Here, the service information database D310 is a database that stores service information. The service information database D310 has a service information table shown in FIG. 4. The information stored in the service information table is not limited to the example shown in FIG. 4, and any fields of the table can be added, changed, or deleted as appropriate.

The services information table shown in FIG. 4A has fields of advertisement ID, facility ID, facility location, facility genres, and advertisement information. The advertisement ID is an ID for identifying the advertisement. The facility ID is an ID identifying the facility that transmits the advertisement, and this ID corresponds to the facilities 20 A-20 C shown in FIG. 1. The facility location is information regarding the location of the facility which transmits the advertisement, and is, for example, location information of the facility. The facility genre is information on the genre of the facility that transmits the advertisement. In the present embodiment, the facility 20A is a medical facility, the facility 20B is a supermarket, and the facility 20C is a pharmacy.

The advertisement information is exemplified in FIG. 4B. For example, the advertisement information of the advertisement A001 transmitted by the institution 20A as a medical facility is "If you suffer from low back pain, please consult."

Such advertisement information is transmitted from the facility-side terminal 200 to the server device 300 by a facility staff or the like inputting the information to the facility-side terminal 200. More specifically, the facility-side terminal 200 has a functional configuration that accepts input of service information including advertisements and transmits the input information to the server device 300. The processor 201 of the facility-side terminal 200 executes a process of transmitting the service information input from the input unit 205 to the server device 300 via the communication unit 206 by a computer program on the main storage unit 202. Then, the service-information obtaining unit F310 obtains the information transmitted from the facility-side terminal 200.

Here, the explanation returns to FIG. 3. The user information obtaining unit F320 obtains predetermined user information (hereinafter, also referred to as "user information") relating to biological information of the user who rides on the vehicle 10. Then, the user information obtaining unit F320 registers the obtained user information in the user information database D320. The biological information of the user is information that can be obtained using the sensor 107, as described above.

The user information database D320 is a database for storing user information. The user information database D320 has a user information table shown in FIG. 5. The information stored in the user information table is not limited to the example shown in FIG. 5, and any fields of the table can be added, changed, or deleted as appropriate.

The user information table shown in FIG. 5 has fields of items representing biological information of the user (a heart rate, a blood pressure, a blood flow, a body temperature, a sweat amount, a body weight, a riding posture) and the state thereof. As can be seen from FIG. 5, in the user information of the present embodiment, the blood flow of the user is poor and the riding posture is bad.

Here, the explanation returns to FIG. 3. The health condition estimating unit F330 estimates the health condition of the user based on the user information obtained by the user information obtaining unit F320 and registered in the user information database D320. In the present embodiment, a user having a relatively heavy body weight takes a bad posture and rides on the vehicle 10, and blood flow of the user is deteriorated. In this instance, the health condition estimating unit F330 can estimate that the user has developed low back pain. At this time, the health condition estimating unit F330 may further obtain interview information from the user and estimate the health condition of the user based on the user information and the interview information. The health condition estimating unit F330 may estimate the health condition of the user based on the user information by using a well-known technique. Then, the health condition estimating unit F330 registers the estimated health condition in the health condition database D330. The health condition database D330 is a database that stores information on the estimated health condition of the user.

The distribution information extracting unit F340 extracts, based on the health condition of the user estimated by the health condition estimating unit F330, information matching the user in the vehicle 10 (hereinafter, sometimes referred to as "distribution information") from the service information regarding the facility (facilities 20 A to 20 C) registered in the service information database D310. The distribution information extracted in this manner is information regarding the medical facility according to the health condition of the user and/or the prescribed store that sells the goods according to the health condition of the user. Here, the distribution information is information that may be actually provided to the user among the service information. In other words, not all of the service information obtained by the service information obtaining unit F310 is actually provided to the user. This will be explained below.

The service information obtaining unit F310 obtains service information of not only the facilities 20 A to 20 C shown in FIG. 1 but also all the facilities using the advertisement providing system 1. If the service information obtaining unit F310 obtains a relatively large number of pieces of service information and all of the pieces of service information are provided to the user, the user may find out information desired by the user from among the large number of pieces of service information, which may be troublesome.

Therefore, the distribution information extracting unit F340 extracts the distribution information based on the health condition of the user. Then, the distribution information extracting unit F340 registers the extracted distribution information in the distribution information database D340.

The distribution information database D340 is a database for storing distribution information. The distribution information database D340 has a distribution information table shown in FIG. 6. The information stored in the distribution information table is not limited to the example shown in FIG. 6, and any fields of the table can be added, changed, or deleted as appropriate.

The distribution information table shown in FIG. 6 is information extracted from the above FIG. 4A and FIG. 4B. As in the above FIG. 4A, it has fields of advertisement ID, facility ID, facility location, facility genres, and advertisement information. In the present embodiment, as described above, it is estimated that the user has developed low back pain by the health condition estimating unit F330. Therefore, in order to prompt the user to treat the low back pain, the distribution information extracting unit F340 extracts, as distribution information, the advertisement A001 and the A003 having the advertisement information related to the treatment of the low back pain, as shown in FIG. 6. That is, the advertisement A001 relating to the treatment of the low back pain, which is the service information transmitted by the medical facility, and the advertisement A003 relating to the treatment device of the low back pain, which is the service information transmitted by the pharmacy, are extracted as the distribution information. The advertisement A001 thus extracted can be referred to as information about the medical facility according to the health condition of the user. Further, the advertisement A003 can be referred to as information about a predetermined store that sells goods according to the user's health condition.

The health condition of the user estimated by the health condition estimating unit F330 is not limited to the above-mentioned low back pain. For example, if jaundice is observed in the image of the user's face sensed by the sensor 107, a medical examination by a doctor is recommended. In this instance, the distribution information extracting unit F340 extracts the service information regarding the medical facility capable of examining jaundice in order to prompt the user to take the examination.

If such information is transmitted from the server device 300 to the on-board device 100 of the vehicle 10, the user can be provided with information that matches the health condition of the user. However, simply providing the distribution information to the user as it is may not sufficiently promote the user to be directed to the facility that transmits the distribution information.

Therefore, as shown in FIG. 3, the server device 300 has a distribution information providing unit F350 as a functional component. The distribution information providing unit F350 selects information to be actually distributed to the user from the distribution information extracted by the distribution information extracting unit F340 based on the position information of the vehicle 10, and transmits the selected distribution information to the on-board device 100 of the vehicle 10 to provide the information to the user. This will be explained with reference to FIG. 7.

Figure 7:
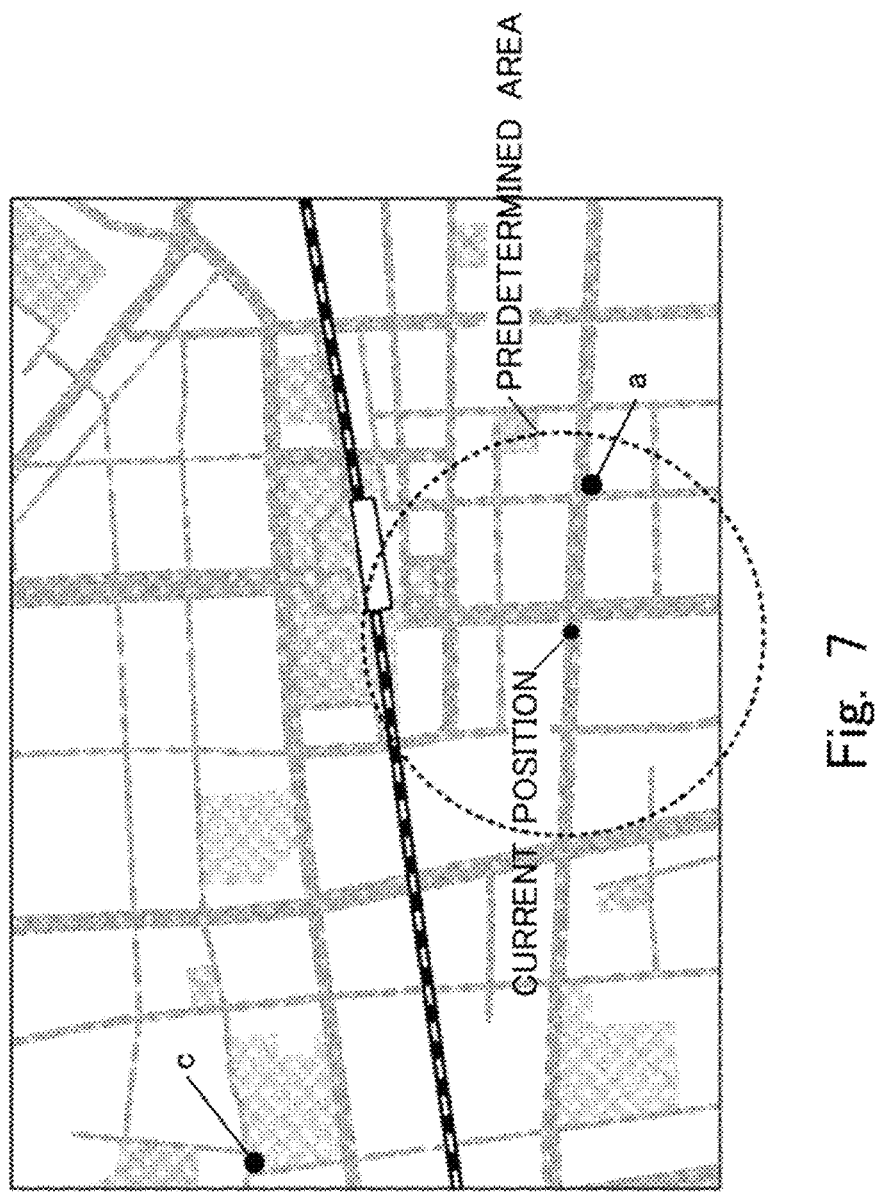
FIG. 7 is a view for explaining a facility to which information is actually provided by a distribution information provision unit among those facilities which send distribution information in a first embodiment.

FIG. 7 is a diagram for explaining a facility, information of which is actually distributed by the distribution information providing unit F350 in the present embodiment. The facility is one of facilities which transmit distribution information thereof. In the present embodiment, the distribution information providing unit F350 selects, from the distribution information extracted by the distribution information extracting unit F340, information on a facility existing within a predetermined area from the current position of the vehicle 10, and provides distribution information on the selected facility to the user.

Figure 8:
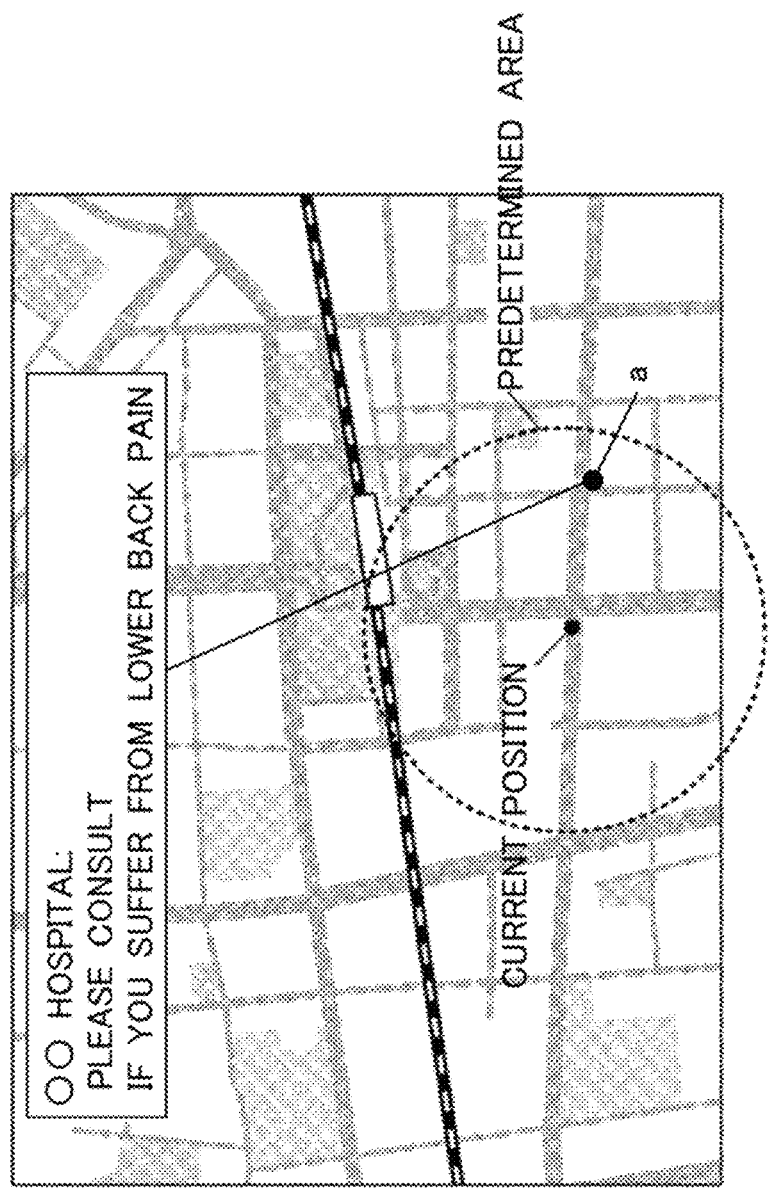
FIG. 8 is a view illustrating an example in which advertisement information of an advertisement to be sent by the facility is displayed on a navigation screen included in the on-board device.

As described above, the distribution information extracting unit F340 extracts the advertisements A001 and A003 shown in FIG. 6 as distribution information. Here, according to FIG. 7, it can be seen that the facility 20A existing at the location a belongs within a predetermined area from the current position of the vehicle 10. The predetermined area can be an area in which the user can relatively easily drop on the way to the destination, and is, for example, an area within 1 km from the current position of the vehicle 10. Then, the distribution information providing unit F350 provides the user with distribution information regarding the facility 20A. More specifically, the distribution information providing unit F350 selects the distribution information (advertisement A001) regarding the facility 20A out of the advertisement A001 and the A003 extracted as the distribution information, and transmits the selected distribution information to the on-board device 100 via the communication unit 304. Then, the processor 101 of the on-board device 100 executes, by the computer program on the main storage unit 102, a process of displaying this information which is received via the communication unit 106 on the display unit 104. FIG. 8 is a diagram illustrating an example in which advertisement information of advertisement A001 transmitted by the facility 20A is displayed on a navigation screen included in the on-board device 100. This provides the user with information that matches the health condition of the user and that relates to a facility that exists in an area where the user can drop in relatively easily. As a result, it is facilitated to direct the user to the facility that transmits the distribution information.

On the other hand, according to FIG. 7, it can be seen that the facility 20C existing at the location c does not belong to a predetermined area from the current position of the vehicle 10. Then, if the vehicle 10 attempts to move from the current position to the facility 20C, the user must move a relatively long distance. Therefore, the distribution information providing unit F350 does not provide the user with the distribution information regarding the facility 20C that does not belong within the predetermined area from the current position of the vehicle 10.

According to the advertisement providing system described above, it is possible to promote to guide the user to a facility that transmits service information matching the health condition of the user.

(Processing Flow)

Figure 9:
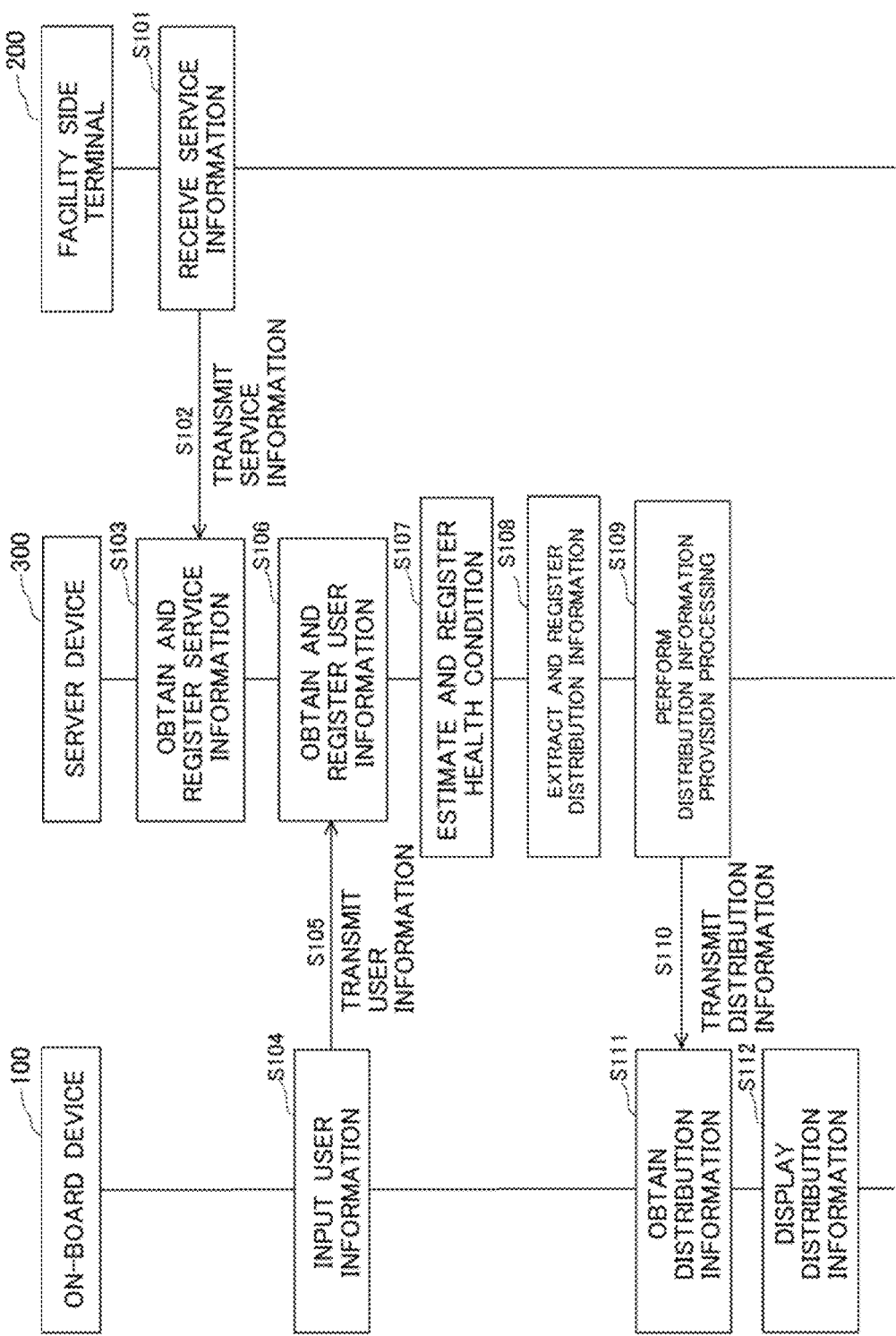
FIG. 9 is a view exemplifying a flow of the operation of the advertisement provision system according to the embodiment.

The flow of the operation of the advertisement providing system according to the present embodiment will be described. FIG. 9 is a diagram illustrating a flow of an operation of the advertisement providing system according to the present embodiment. FIG. 9 explains the flow of operations among the respective components and the processing executed by the respective components in the advertisement providing system 1.

The facility-side terminal 200 receives service information from the staff of the facility or the like (S101), and transmits the service information to the server device 300 (S102).

The server device 300 obtains the service information transmitted from the facility-side terminal 200 via reception by the communication unit 304, and registers the service information in the service information database D310 (S103).

User information is input to the on-board device 100 (S104). In the present embodiment, in the S104 process, the biological information of the user riding on the vehicle 10 is inputted by the sensor 107. Then, the on-board device 100 transmits the user information to the server device 300 (S105).

The server device 300 obtains the user information transmitted from the on-board device 100 via reception by the communication unit 304, and registers the user information in the user information database D320 (S106).

Then, the server device 300 estimates the health condition of the user based on the user information, and registers the estimated health condition in the health condition database D330 (S107). Then, the server device 300 extracts, from the service information, the distribution information determined to match the user based on the user's health condition, and registers the distribution information in the distribution information database D340 (S108). Note that such distribution information is information regarding a medical facility according to the health condition of the user and/or a predetermined store that sells goods according to the health condition of the user.

Further, the server device 300 executes a process of providing distribution information to the user (distribution information providing process) based on the position information of the vehicle 10 (S109). In the present embodiment, in the distribution information providing process, the server device 300 obtains the current position of the vehicle 10. Here, the server device 300 obtains the current position of the vehicle 10 by receiving the current position of the vehicle 10 obtained by the position information obtaining unit 108 and transmitted from the on-board device 100 via the communication unit 106. In the distribution information providing process, distribution information to be actually provided to the user is selected out of the distribution information registered in the distribution information database D340 so that distribution information regarding facilities existing within a predetermined area from the current position of the vehicle 10 is provided to the user, and the selected distribution information is transmitted to the on-board device 100 (S110).

The on-board device 100 obtains the distribution information transmitted from the server device 300 (S111). Then, the on-board device 100 executes a process of displaying the obtained distribution information on the display unit 104 (S112). This provides the user with information that matches the health condition of the user and distribution information regarding facilities that exist in an area where the user can relatively easily drop in.

Here, in the above description, the case where only the facility 20A exists within the predetermined area from the current position of the vehicle 10 has been described, but the present disclosure is not intended to be limited thereto. If the facility 20A and the facility 20C exist within the predetermined area from the current position of the vehicle 10, distribution information regarding the facility 20A and the facility 20C is transmitted to the on-board device 100. In this case, the on-board device 100 can display the distribution information regarding the facility 20A and the facility 20C on the display unit 104. Then, the user can select a facility to visit on the way to the destination after looking at the advertisement A001 transmitted by the facility 20A and the advertisement A003 transmitted by the facility 20C, which are displayed on the display unit 104.

(Recording Medium)

A program for causing a computer or other machine or device (hereinafter referred to as a computer or the like) to realize any of the functions described above can be recorded on a recording medium readable by the computer or the like. The function can be provided by causing a computer or the like to read and execute a program of the recording medium.

Here, a computer-readable recording medium refers to a non-temporary recording medium in which information such as data and a program is accumulated by electrical, magnetic, optical, mechanical, or chemical action and can be read from a computer or the like. Among such recording media, there are, for example, flexible disks, magneto-optical disks, CD-ROM's, CD-R/W's, DVDs, Blu-ray disks, DATs, 8 mm magnetic tapes, memory cards such as flash memories, and the like. As a recording medium fixed to a computer or the like, there are a hard disk, a read only memory (ROM), and the like. Further, the Solid State Drive can be used as a recording medium detachable from a computer or the like, or as a recording medium fixed to the computer or the like.

Second Embodiment

Next, a second embodiment of the present disclosure will be described. In the present embodiment, the detailed descriptions of the component and control processing which are substantially the same as those of the first embodiment are omitted.

In the above-described first embodiment, the distribution information providing unit F350 of the server device 300 selects information regarding a facility existing within a predetermined area from the current position of the vehicle 10 out of the distribution information extracted by the distribution information extracting unit F340, and provides the selected distribution information regarding the facility to the user. On the other hand, in the present embodiment, the distribution information providing unit F350 of the server device 300 selects information on a facility existing on a predetermined travel route of the vehicle 10 out of the distribution information extracted by the distribution information extracting unit F340, and provides the user with the selected distribution information regarding the facility. This will be explained with reference to FIG. 10.

Figure 10:
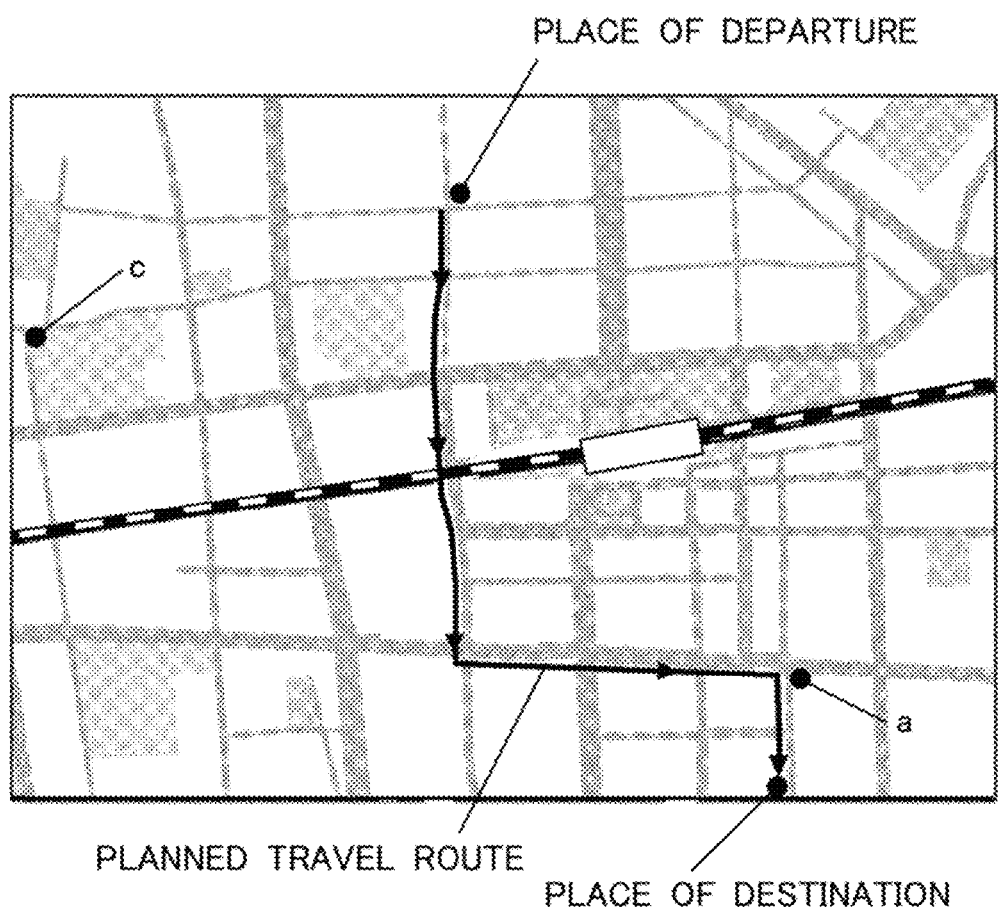
FIG. 10 is a view for explaining a facility to which information is actually provided by a distribution information provision unit among those facilities which send distribution information in a second embodiment.

FIG. 10 is a diagram for explaining a facility, information of which is actually provided by the distribution information providing unit F350 in the present embodiment. The facility is one of facilities which transmit distribution information thereof. When the user inputs a place of departure and a place of destination of the vehicle 10 to the navigation system included in the on-board device 100 as the position information of the vehicle 10, the planned travel route of the vehicle 10 shown in FIG. 10 is set in advance.

According to FIG. 10, it can be seen that the facility 20A existing at the location a is located on the travel route of the vehicle 10. On the other hand, it can be seen that the facility 20C existing at the location c is not located on the planned travel route of the vehicle 10. In this instance, the distribution information providing unit F350 provides the user with distribution information regarding the facility 20A. In doing so, the user can relatively easily drop in the facility that transmits service information according to his/her health condition on the way to the destination.

The above-described advertisement providing system can also promote to guide the user to a facility that transmits service information according to the user's health condition.

It should be noted that the distribution information providing unit F350 may select the distribution information regarding the facility existing on the predetermined travel route of the vehicle 10 out of the distribution information extracted by the distribution information extracting unit F340, and provide the distribution information regarding the selected facility to the user. Furthermore, the distribution information providing unit F350 may obtain the current position of the vehicle 10 during the movement of the vehicle 10, select the distribution information regarding the facility existing within a predetermined area from the current position of the vehicle 10, and further provide the selected distribution information regarding the facility to the user.

Other Embodiments

The above embodiment is merely an example, and the present disclosure can be implemented by appropriately changing it within a range not deviating from the gist thereof.

The processes and means described in the present disclosure may be freely combined and embodied to the extent that no technical conflicts exist.

Furthermore, a process that is described to be performed by one device may be shared and performed by a plurality of devices. Processes described to be performed by different devices may be performed by one device. Which function is to be implemented by which hardware configuration (server configuration) in a computer system may be flexibly changed.

The present disclosure may also be implemented by supplying computer programs for implementing the functions described in the embodiments described above to a computer, and by one or more processors of the computer reading out and executing the programs. Such computer programs may be provided to the computer by a non-transitory computer-readable storage medium that can be connected to a system bus of the computer, or may be provided to the computer through a network. The non-transitory computer-readable storage medium may be any type of disk including magnetic disks (floppy (registered trademark) disks, hard disk drives (HDDs), etc.) and optical disks (CD-ROMs, DVD discs, Blu-ray discs, etc.), read-only memories (ROMs), random access memories (RAMs), EPROMs, EEPROMs, magnetic cards, flash memories, optical cards, and any type of medium suitable for storing electronic instructions.

What is claimed is:

1. An information processing device including a controller comprising at least one processor configured to execute:
    receiving, via a communication unit, predetermined service information transmitted from a facility-side terminal operated by a user at a facility and including an advertisement of the facility input by the user on the facility-side terminal;
    receiving, via the communication unit, predetermined user information on biological information of a user in a vehicle in which the user rides, the user information being obtained via a sensor in the vehicle and transmitted from the vehicle;
    estimating a health condition of the user based on the user information;
    extracting distribution information which is information, among the service information, judged to match the user based on the user's health condition, and which is information about the facility as a medical facility according to the health condition or/and information about the facility as a predetermined store which sells goods according to the user's health condition;
    receiving, via the communication unit, a current position of the vehicle obtained via a GPS receiver in the vehicle and transmitted from the vehicle;
    selecting, based on position information of the vehicle including the current position of the vehicle thus received, information about the medical facility or/and the predetermined store existing within an area within a predetermined distance from the current position of the vehicle as information to be actually distributed to the user from among the distribution information thus extracted; and
    providing the information thus selected to the user, by transmitting the selected distribution information to an on-board device of the vehicle, wherein
    the distribution information thus extracted and the distribution information thus selected include the advertisement of the medical facility or/and the advertisement of the predetermined store.

2. The information processing device as set forth in claim 1, wherein
the position information further includes a place of departure and a place of destination of the vehicle; and
the controller selects, from among the extracted distribution information, information about the medical facility or/and the predetermined store existing within the area within the predetermined distance from the current position of the vehicle and existing on a planned travel route of the vehicle which has been set in advance.

3. The information processing device as set forth in claim 1, wherein
the information processing device stores in a memory:
a first database that stores received predetermined service information transmitted from a plurality of facility-side terminals each operated by a user at a respective facility, and
a second database that stores received predetermined user information transmitted from a plurality of vehicles on biological information of each user riding in a respective vehicle.

4. An information processing method in which a computer executes:
a step of receiving, via a communication unit, predetermined service information transmitted from a facility-side terminal operated by a user at a facility and including an advertisement of the facility input by the user on the facility-side terminal;
a step of receiving, via the communication unit, predetermined user information on biological information of a user in a vehicle in which the user rides, the user information being obtained via a sensor in the vehicle and transmitted from the vehicle;
a step of estimating a health condition of the user based on the user information;
a step of extracting distribution information which is information, among the service information, judged to match the user based on the user's health condition, and which is information about the facility as a medical facility according to the health condition or/and information about the facility as a predetermined store which sells goods according to the user's health condition;
a step of receiving, via the communication unit, a current position of the vehicle obtained via a GPS receiver in the vehicle and transmitted from the vehicle;
a step of selecting, based on position information of the vehicle including the current position of the vehicle thus received, information about the medical facility or/and the predetermined store existing within an area within a predetermined distance from the current position of the vehicle as information to be actually distributed to the user from among the distribution information thus extracted; and
a step of providing the information thus selected to the user, by transmitting the selected distribution information to an on-board device of the vehicle, wherein
the distribution information thus extracted and the distribution information thus selected include the advertisement of the medical facility or/and the advertisement of the predetermined store.

5. A non-transitory storage medium having a program stored thereon, the program being configured to make a computer execute:
a step receiving, via a communication unit, predetermined service information transmitted from a facility-side terminal operated by a user at a facility and including an advertisement of the facility input by the user on the facility-side terminal;
a step of receiving, via the communication unit, predetermined user information on biological information of a user in a vehicle in which the user rides, the user information being obtained via a sensor in the vehicle and transmitted from the vehicle;
a step of estimating a health condition of the user based on the user information;
a step of extracting distribution information which is information, among the service information, judged to match the user based on the user's health condition, and which is information about the facility as a medical facility according to the health condition or/and information about the facility as a predetermined store which sells goods according to the user's health condition;
a step of receiving, via the communication unit, a current position of the vehicle obtained via a GPS receiver in the vehicle and transmitted from the vehicle;
a step of selecting, based on position information of the vehicle including the current position of the vehicle thus received, information about the medical facility or/and the predetermined store existing within an area within a predetermined distance from the current position of the vehicle as information to be actually distributed to the user from among the distribution information thus extracted; and
a step of providing the information thus selected to the user, by transmitting the selected distribution information to an on-board device of the vehicle, wherein
the distribution information thus extracted and the distribution information thus selected include the advertisement of the medical facility or/and the advertisement of the predetermined store.

* * * * *